(12) United States Patent
MacLean

(10) Patent No.: US 7,637,860 B2
(45) Date of Patent: Dec. 29, 2009

(54) DEVICES FOR MINIMALLY INVASIVE PELVIC SURGERY

(75) Inventor: Brian MacLean, Acton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 649 days.

(21) Appl. No.: 11/280,889

(22) Filed: Nov. 16, 2005

(65) Prior Publication Data

US 2007/0123746 A1    May 31, 2007

(51) Int. Cl.
*A61F 2/02* (2006.01)
(52) U.S. Cl. .......................... 600/29; 600/37
(58) Field of Classification Search ............. 600/12–13, 600/29–30, 37; 128/897–899; 403/27
See application file for complete search history.

(56) References Cited

U.S. PATENT DOCUMENTS

| | | | |
|---|---|---|---|
| 4,762,131 A * | 8/1988 | Okuda ........................ | 607/88 |
| 4,798,193 A | 1/1989 | Giesy et al. | |
| 4,824,435 A | 4/1989 | Giesy et al. | |
| 5,337,736 A | 8/1994 | Reddy | |
| 5,439,467 A | 8/1995 | Benderev et al. | |
| 5,500,000 A | 3/1996 | Feagin et al. | |
| 5,582,188 A | 12/1996 | Benderev et al. | |
| 5,766,221 A | 6/1998 | Benderev et al. | |
| 5,899,909 A | 5/1999 | Claren et al. | |
| 5,987,715 A * | 11/1999 | Khon ........................ | 24/303 |
| 5,988,171 A * | 11/1999 | Sohn et al. .................. | 128/848 |
| 6,042,534 A | 3/2000 | Gellman et al. | |
| 6,042,536 A | 3/2000 | Tihon et al. | |
| 6,099,547 A | 8/2000 | Gellman et al. | |
| 6,110,101 A | 8/2000 | Tihon et al. | |
| 6,273,852 B1 | 8/2001 | Lehe et al. | |
| 6,406,423 B1 | 6/2002 | Scetbon | |
| 6,475,139 B1 | 11/2002 | Miller | |
| 6,478,727 B2 | 11/2002 | Scetbon | |
| 6,494,887 B1 | 12/2002 | Kaladelfos | |
| 6,592,515 B2 | 7/2003 | Thierfelder et al. | |
| 6,596,001 B2 | 7/2003 | Stormby et al. | |
| 6,612,977 B2 | 9/2003 | Staskin et al. | |
| 6,641,524 B2 | 11/2003 | Kovac | |
| 6,648,921 B2 | 11/2003 | Anderson et al. | |
| 6,652,450 B2 | 11/2003 | Neisz et al. | |
| 6,666,817 B2 | 12/2003 | Li | |

(Continued)

FOREIGN PATENT DOCUMENTS

GB    2353220    10/2000

(Continued)

OTHER PUBLICATIONS

International Preliminary Report on Patentability for International Application No. PCT/US2006/044656 dated May 20, 2008.

*Primary Examiner*—Charles A Marmor, II
*Assistant Examiner*—Sehar Mehmood
(74) *Attorney, Agent, or Firm*—Bingham McCutchen LLP

(57) ABSTRACT

Systems and methods employing a sling delivery assembly having a sling delivery device couplable to a sling assembly to deliver an implant through a transobturator incision point are disclosed. Successful coupling between the sling delivery device and the sling assembly can be verified through changes in an optical or electrical signal produced at the coupling location.

22 Claims, 8 Drawing Sheets

U.S. PATENT DOCUMENTS

| | | |
|---|---|---|
| 6,685,629 B2 | 2/2004 | Therin |
| 6,911,003 B2 | 6/2005 | Anderson et al. |
| 6,936,052 B2 | 8/2005 | Gellman et al. |
| 7,048,682 B2 * | 5/2006 | Neisz et al. .................... 600/30 |
| 7,291,104 B2 * | 11/2007 | Neisz et al. .................... 600/30 |
| 7,393,320 B2 * | 7/2008 | Montpetit et al. ............. 600/30 |
| 2002/0099258 A1 | 7/2002 | Staskin et al. |
| 2002/0128670 A1 | 9/2002 | Ulmsten et al. |
| 2003/0004395 A1 | 1/2003 | Therin |
| 2003/0009181 A1 | 1/2003 | Gellman et al. |
| 2003/0023138 A1 | 1/2003 | Luscombe |
| 2003/0036676 A1 | 2/2003 | Scetbon |
| 2003/0098221 A1 * | 5/2003 | Bhusri et al. ............. 200/43.01 |
| 2003/0149440 A1 | 8/2003 | Kammerer et al. |
| 2003/0171644 A1 | 9/2003 | Anderson et al. |
| 2003/0225424 A1 | 12/2003 | Benderev |
| 2004/0039246 A1 | 2/2004 | Gellman et al. |
| 2004/0073234 A1 | 4/2004 | Chu et al. |
| 2004/0087970 A1 * | 5/2004 | Chu et al. ................... 606/119 |
| 2004/0102808 A1 | 5/2004 | Voss |
| 2004/0106846 A1 | 6/2004 | Gellman |
| 2004/0116944 A1 | 6/2004 | Chu et al. |
| 2004/0122474 A1 | 6/2004 | Gellman et al. |
| 2004/0133217 A1 | 7/2004 | Watschke |
| 2004/0153102 A1 | 8/2004 | Therin et al. |
| 2004/0225181 A1 | 11/2004 | Chu et al. |
| 2004/0230206 A1 | 11/2004 | Gellman et al. |
| 2004/0243166 A1 | 12/2004 | Odermatt et al. |
| 2005/0021086 A1 | 1/2005 | De Leval |
| 2005/0027368 A1 | 2/2005 | Hellhammer et al. |
| 2005/0038451 A1 | 2/2005 | Rao et al. |
| 2005/0090706 A1 | 4/2005 | Gellman et al. |
| 2005/0240076 A1 | 10/2005 | Neisz et al. |

FOREIGN PATENT DOCUMENTS

| | | |
|---|---|---|
| WO | WO-98/35616 | 8/1998 |
| WO | WO-99/37216 | 7/1999 |
| WO | WO-01/30246 | 5/2001 |
| WO | WO-02/30293 | 4/2002 |
| WO | WO-02/062237 | 8/2002 |
| WO | WO-03/096928 | 5/2003 |
| WO | WO-03/096930 | 11/2003 |
| WO | WO-2004/086983 | 10/2004 |

* cited by examiner

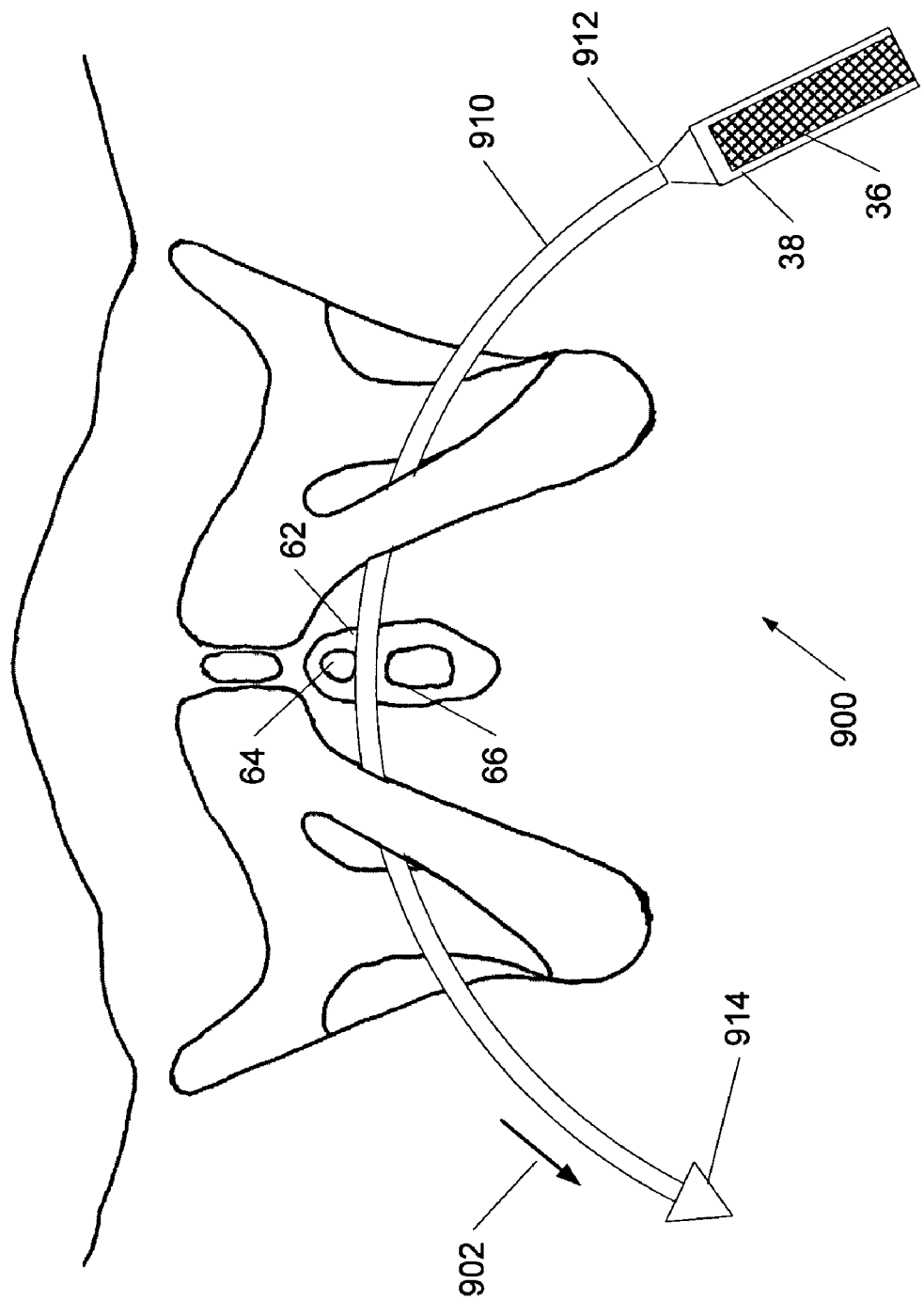

DEVICES FOR MINIMALLY INVASIVE PELVIC SURGERY

FIELD OF THE INVENTION

The invention generally relates to systems and methods for delivering an implantable sling to an anatomical location in a patient. In various embodiments, the invention is directed to systems and methods relating to the use of a segmented or continuous sling delivery device for delivering an implantable sling.

BACKGROUND OF THE INVENTION

Anatomical tissues may become weakened or damaged by age, injury, or disease. This decrease in the structural integrity of anatomical tissues may have significant medical consequences. Even in the absence of tissue necrosis, weakening of an anatomical structure may impair one or more of the biological functions of the tissue. To help alleviate this impact on biological function, implantable, supportive slings have been developed. These slings can be implanted into a patient to provide support for the weakened or damaged tissue. The support provided by the sling mimics the natural position and structure of the tissue, and thereby helps decrease or eliminate impairment of biological function resulting from tissue weakening or damage. Although supportive slings have been used in numerous contexts to address the weakening of a variety of anatomical tissues, they have proven particularly useful for decreasing urinary incontinence resulting from weakening or damage to urethral, periurethral and/or bladder tissue.

Stress urinary incontinence (SUI) affects primarily women, but also men, and is generally caused by two conditions, intrinsic sphincter deficiency (ISD) and hypermobility. These conditions may occur independently or in combination. In ISD, the urinary sphincter valve, located within the urethra, fails to close properly (coapt), causing urine to leak out of the urethra during stressful activity. Hypermobility is a condition in which the pelvis floor is distended, weakened, or damaged, causing the bladder neck and proximal urethra to rotate and descend in response to increases in intra-abdominal pressure (e.g., due to sneezing, coughing, straining, etc.). As a result, the patient's response time becomes insufficient to promote urethral closure and, consequently, the patient suffers from urine leakage and/or flow. SUI has a variety of causes including, but not limited to, pregnancy, aging, infection, injury, congenital defect, and disease.

One way to treat SUI involves placing an implantable sling under the bladder neck or the mid-urethra to provide a urethral platform. Placement of the sling limits the endopelvis fascia drop. There are various methods for placing the sling. Slings can be affixed and stabilized using traditional bone anchoring approaches, as well as recently developed anchorless methods. Additionally, a variety of implantation procedures, including various routes of administration, exist. These procedures provide physicians with a range of implantation options. Physicians can readily select amongst the various implantation procedures based on numerous patient-specific factors including, but not limited to, age, gender, overall health, location of tissue defect, the degree of tissue impairment, and the like. Furthermore, physicians can select from amongst numerous sling delivery devices that facilitate sling placement.

Despite the numerous advances in sling design, implantation methodologies, and delivery devices, no single method and/or device is appropriate for every situation. Accordingly, devices, systems, and methods that offer new approaches for sling implantation would be advantageous to the medical community. In particular, it would be desirable to have a sling application device that does not require a transvaginal incision and/or excessive dilation of the tissue between the urethra and the vaginal wall, thereby reducing surgical trauma.

SUMMARY OF THE INVENTION

The invention addresses deficiencies of the prior art by providing devices, systems and methods for facilitating delivery of an implant to an anatomical site. According to a preferred embodiment, the device can be used to deliver an implant, such as a sling for treating urinary incontinence, to a mid-urethral location of a patient. The methods and systems of the invention simplify the delivery of the implant by using a segmented sling delivery assembly with a sling delivery device and a sling assembly which can be reliably connected at a suburethral location without a transvaginal incision.

In one aspect of the invention, a sling delivery assembly includes a delivery device having a guide tube with a proximal end and a distal end, a shaft slidingly interfitted in the guide tube, and a first connector attached to or integrally formed with the distal end of the guide tube. The sling delivery assembly further includes a sling assembly having a proximal end and a distal end, and a second connector attached to or integrally formed with the distal end of the sling assembly and adapted for interlocking engagement with the first connector. An indicator is formed in or on the first or second connector, or both, to indicate interlocking engagement between the first and second connector.

In another aspect of the invention, a sling delivery assembly includes a delivery device having a shaft with a proximal end and a distal end, and a first connector attached to or integrally formed with the distal end of the shaft. The sling delivery assembly further includes a sling assembly having a dilator tube with proximal end and a distal end and a lumen, a sling or sleeve attached to the proximal end of the dilator, and a second connector attached to or integrally formed with the distal end of the dilator. The second connector is adapted for interlocking engagement with the first connector. An indicator is formed in or on the first or second connector, or both, to indicate engagement between the first and second connector.

In one embodiment, the sling delivery assembly may also include a pusher assembly having a pusher shaft with a pusher tip. The pusher shaft slidingly interfits inside the lumen of the dilator. The pusher assembly further includes a pusher tube having a distal end adapted to make contact with the proximal end of the dilator tube for moving the pusher tip into a retracted position inside the lumen of the dilator tube, to enable engagement between the first and second connector.

According to another aspect of the invention, a method of treating urinary incontinence by implanting a surgical sling into the body of a patient without a transvaginal incision includes the steps of inserting a sling assembly having a sling associated therewith through a first transobturator incision point of a patient, inserting a delivery device couplable to the sling assembly through a second contralateral transobturator incision point of a patient, engaging the delivery device with the sling assembly at a connection location, verifying interlocking engagement between the delivery device and the sling assembly through a change in an optical or electrical signal produced at the connection location, and pulling the interlocked delivery device and sling assembly through the periurethral tissue of the patient.

Embodiments of the invention may include a delivery device having a tissue dissector to facilitate piercing the transobturator membrane and pelvic tissue. The delivery device may have a handle disposed on the proximate end of the delivery device and an actuator disposed on or in the handle for causing the dilator tip or tissue dissector to protrude from and retract into a distal end of the guide tube. The shaft of the delivery device may be curved or have any other shape suitable for the procedure.

The indicator may include optical elements, such as a light emitter disposed on one of the first or second connectors, and an optically transmissive element formed on the other connector, wherein an observed color of light emitted from the light emitter changes upon engagement between the first and second connector. Alternatively or in addition, the indicator may include an electrical element, such as a resistive element disposed on one of the first or second connectors, and a contact pad formed on the other connector and contacting the resistive element upon engagement between the first and second connector. Instead of closing an electrical connection between the first and second connector, one of the connectors may include an electrical switch which is mechanically actuated upon engagement between the first and second connector.

Electrical indicators may also include an inductive or a capacitive element disposed on one of the first or second connectors, and a sensor disposed on the other connector and detecting a change in an inductance or capacitance upon engagement between the first and second connector.

The connectors may include a mechanical and/or magnetic interlocking mechanism.

Other aspects and advantages of the invention are described below.

BRIEF DESCRIPTION OF THE DRAWINGS

The following figures depict illustrative embodiments of the invention in which like reference numerals refer to like elements. These depicted embodiments may not be drawn to scale and are to be understood as illustrative of the invention and not as limiting in any way.

FIG. 9 shows another embodiment of a single piece delivery assembly.

DESCRIPTION OF EMBODIMENTS

As described above in summary, the invention in various illustrative embodiments is directed to systems, devices, and methods employing a delivery device, which can be segmented or in one piece, to deliver a sling to the periurethral tissues of a patient. The delivery device of the present invention may inserted in the ischiopubic region and passed through an obturator foramen, without making a transvaginal incision.

Figure 1:
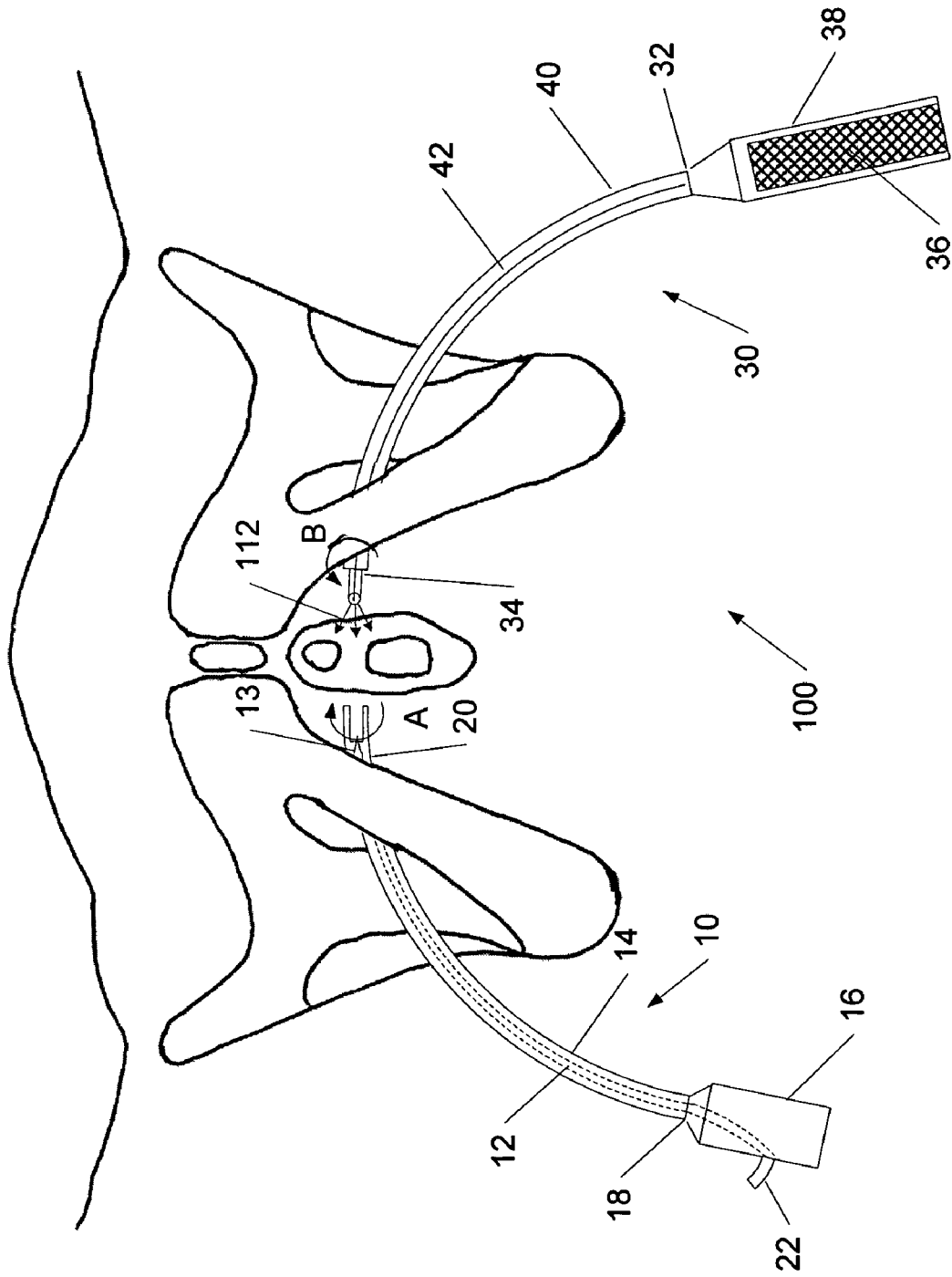
FIG. 1 shows a perspective front view of one embodiment of a sling delivery assembly according to the invention.

FIG. 1 shows a perspective front view of one embodiment of a cooperating sling delivery assembly 100 according to the invention. As shown, the cooperating sling delivery assembly 100 in accordance with one aspect of the present invention includes a delivery device 10 and a sling assembly 30. The delivery device 10 includes a shaft 12, which may have a needle-shaped or blunt tip 13, a guide tube 14, and a handle 16. The proximal end 18 of the guide tube 14 may be attached to the distal part of the handle 16 in any variety of manners, including brazing, threading or other means well known to those of skill in the art. Preferably, handle 16 is provided with knurling or other surface texturing to produce a high friction gripping surface. In this particular embodiment, both the shaft 12 and the guide tube 14 are attached to the handle 16. The guide tube 14 has a proximal end 18 and a distal end 20, and can also function as a dilator tube. A tubular member or wall of the guide tube 14 forms a lumen that allows the shaft 12 to slideably move inside the guide tube 14. The guide tube 14 may be made of stainless steel or plastic. In one embodiment, the guide tube 14 may be made of the same material as the shaft 12. The distal end 20 of the guide tube 14 is marked by a circular arrow "A" to indicate that it may include a connector of the type described in more detail below.

Figure 2:
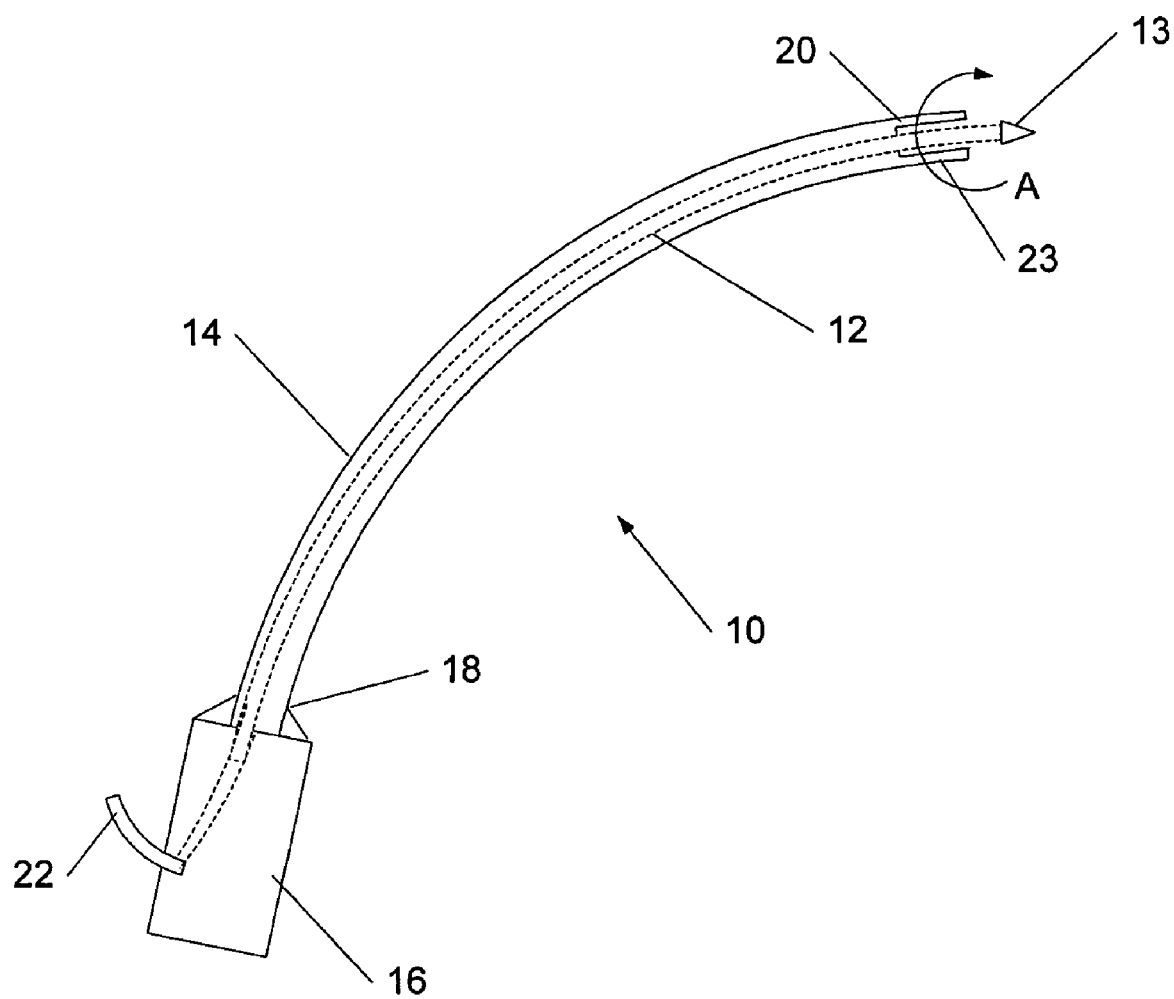
FIG. 2 shows the delivery device of the sling delivery assembly of FIG. 1.

As shown more clearly in FIG. 2, the handle 16 includes an actuator 22 operatively connected to the proximal end 18 of the guide tube 14. The connection between the actuator 22 may be permanent or reversible (removable and reusable). The illustrative actuator 22 operates through a mechanical interconnection. However, in alternative embodiments, the actuator 22 may operate through electrical, chemical, magnetic, piezoelectric or other suitable mechanism, separately or in combination. The dissection tip 13 can be extended from and retracted into the lumen at the distal end 20 of shaft 12 by manipulating actuator 22, such as a lever or slider, or another suitable element disposed on the handle.

The guide tube 14 in the depicted illustrative embodiment has approximately the shape of a partial circle, for example between an eighth and a quarter circle, and a length of between about 6 inches (15 cm) to about 10 inches (25 cm) in length. However, the dimensions and shape of the guide tube and the associated shaft may have any other suitable shape, such as curved and straight sections, depending on anatomical considerations and the type of procedure in which it is intended to be used. In FIG. 1, the actuator 22 is shown at its proximal position, so that the distal end of the shaft and hence also the tip 13 is withdrawn into the guide tube. Conversely, in FIG. 2, the actuator 22 is at its distal position, so that the tip 13 of the shaft 12 protrudes from the distal end 20 of the guide tube, for example, by about 0.25 to 1 inch, for piercing and/or dissecting tissue and membranes.

Figure 4:
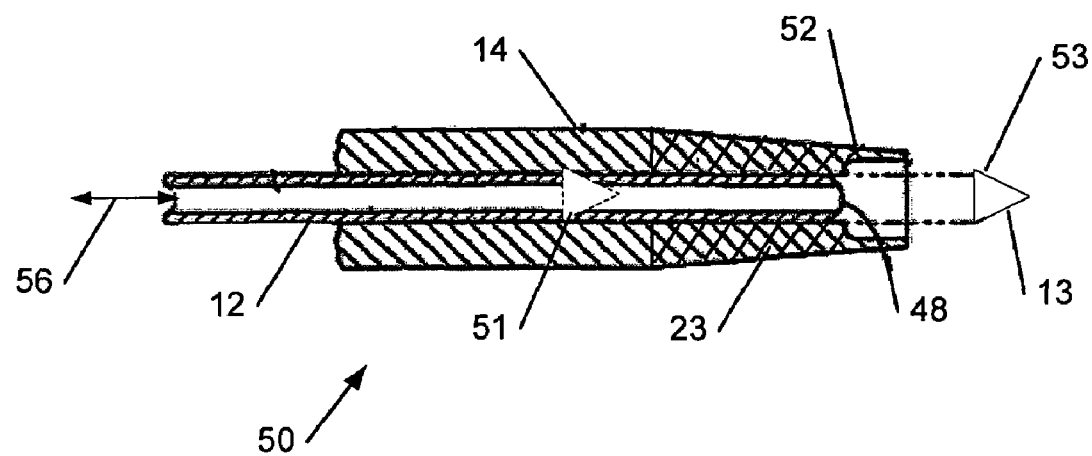
FIG. 4 shows a connector for the delivery device of FIG. 2.

The distal end 20 of the guide tube 14 may also include a translucent sleeve portion 23 which can provide the physician with an indication if the delivery section 10 is properly connected with the sling assembly 30 in the suburethral tissue, as will be described in more detail below with reference to FIGS. 4 and 6.

Figure 3:
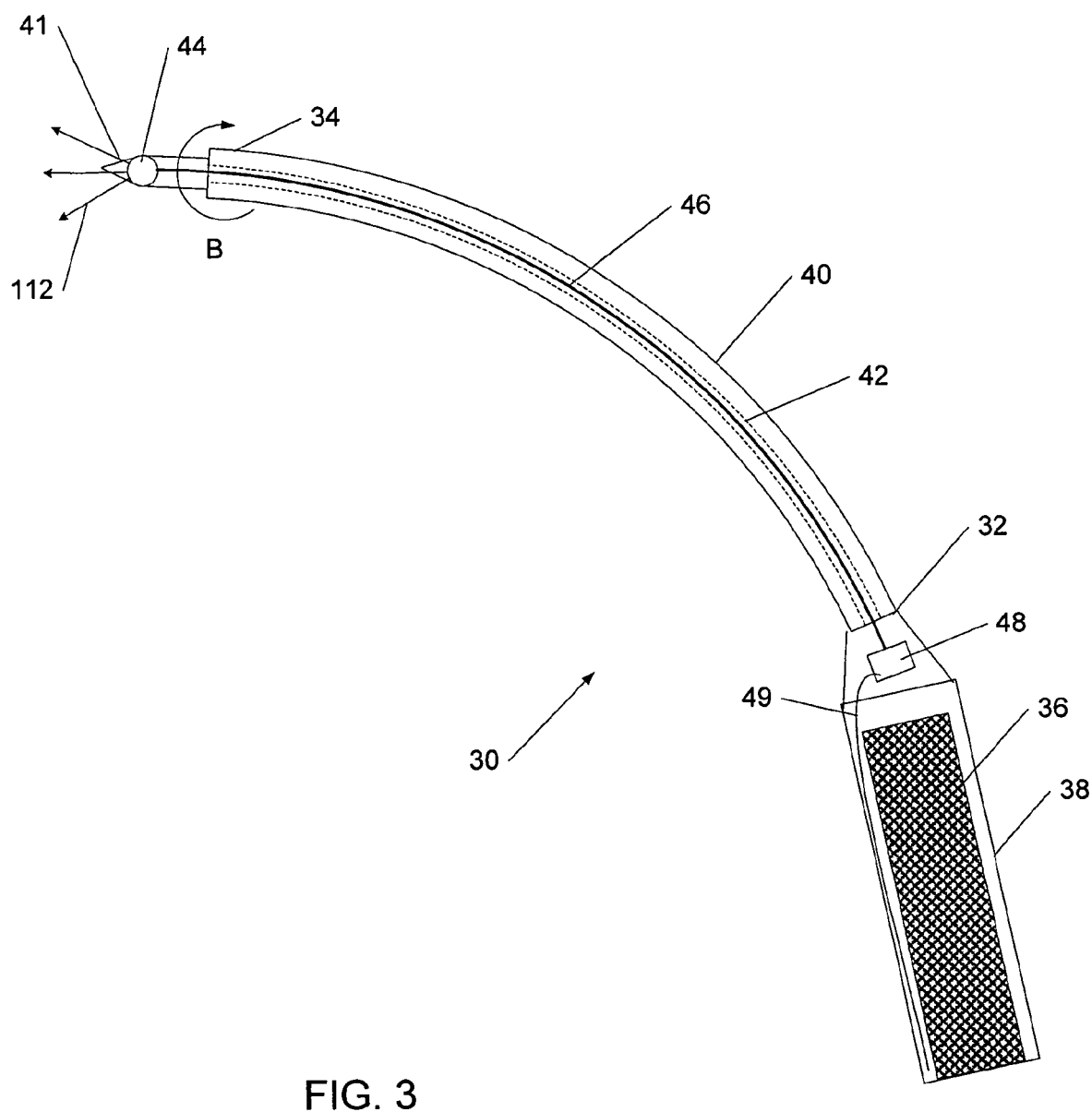
FIG. 3 shows the sling assembly of the sling delivery assembly of FIG. 1.

FIG. 3 shows in more detail the sling assembly 30 of FIG. 1. The sling assembly 30 has a proximal end 32 and a distal end 34. The sling assembly 30 includes a sling or mesh 36 which may or may not be enclosed in or at least partially covered by a sleeve 38. The sling 36 is typically free floating inside the sleeve 38, if a sleeve 38 is employed.

The sling 36 used with the invention may be fabricated from any suitable material(s), preferably biocompatible materials. In certain illustrative embodiments, the material may include, for example, synthetic mesh or other synthetic material; it may also or alternatively include non-synthetic material, such as cadaver, human or animal tissue; it may also include any combinations thereof. In examples employing synthetic material for the sling 36, it may be derived from any suitable synthetic material. Such material could include, for example, polymeric material such as, for example, Polytetrafluorethylene (GORE-TEX®), polypropylene (MARLEX®), polyethylene (MERSILINE®), silastic, or impregnated collagen matrix (PROTEGEN™).

Other suitable synthetic materials for the sling 36 may include, for example, nylon, polyethylene, polyester, polypropylene, fluoropolymers, copolymers thereof, combinations thereof, or other suitable synthetic material(s). The material may be a synthetic material that is absorbable by the patient's body. Suitable absorbable synthetic materials can include polyglycolic acid, polylactic acid, and other suitable absorbable synthetic materials. The filament mesh sling 36 material may be fabricated from one or more yarns, which yarns may be made from one or more materials.

Alternatively, the materials for the sling 36 may employ non-synthetic or natural materials, for example materials from human fascia, cadaveric fascia, or other mammalian tissue(s). Human tissues may be used in certain embodiments and may be derived, for example, from human cadaveric or engineered human tissue. Animal tissues may be derived, for example, from porcine, ovine, bovine, and equine tissue sources. In certain embodiments the materials for the sling 36 may include a combination of non-synthetic (e.g., mammalian tissue(s)) and synthetic materials.

According to a further illustrative embodiment, any or all of the sling 36 may be configured to be biodegradable/bioabsorbable. According to another feature, at least a portion of the sling 36 is biodegradable and may also dissolve and/or be absorbed into the patient's tissues. For example, in some embodiments, only a section of the sling 12 is biodegradable/bioabsorbable, such as, for example, an intermediate portion. Examples of biodegradable/bioabsorbable materials that may be used for the sling 36 include, without limitation, polylactic acid (PLA), polyglycolic acid (PGA), poly-L-lactic acid (PLLA), human dermis and decellularized animal tissue.

Exemplary biodegradable/bioabsorbable materials, in addition to those listed above, which may be employed for the sling 12 include, but are not limited to, polylactic acid, polyglycolic acid and copolymers and mixtures thereof, such as poly(L-lactide) (PLLA), poly(D,L-lactide) (PLA), polyglycolic acid [polyglycolide (PGA)], poly(L-lactide-co-D,L-lactide) (PLLA/PLA), poly(L-lactide-co-glycolide) (PLLA/PGA), poly(D,L-lactide-co-glycolide) (PLA/PGA), poly(glycolide-co-trimethylene carbonate) (PGAIPTMC), poly(D,L-lactide-co-caprolactone) (PLA/PCL), and poly(glycolide-co-caprolactone) (PGA/PCL); polyethylene oxide (PEO); polydioxanone (PDS); polypropylene fumarate; polydepsipeptides, poly(ethyl glutamate-co-glutamic acid), poly(tert-butyloxy-carbonylmethyl glutamate); polycaprolactone (PCL), poly(hydroxy butyrate), polycaprolactone co-butylacrylate, polyhydroxybutyrate (PHBT) and copolymers of polyhydroxybutyrate; polyphosphazenes, poly(phosphate ester); maleic anhydride copolymers, polyiminocarbonates, poly[(97.5% dimethyl-trimethylene carbonate)-co-(2.5% trimethylene carbonate)], cyanoacrylate, hydroxypropylmethylcellulose; polysaccharides, such as hyaluronic acid, chitosan and regenerate cellulose; poly(amino acid) and proteins, such as gelatin and collagen; and mixtures and copolymers thereof.

According to a further illustrative embodiment, the sling 36 may incorporate, be coated or otherwise treated with one or more agents for providing a therapeutic effect, for example, to reduce discomfort, to reduce the chance of infection and/or to promote tissue growth. In some embodiments, the agent may be configured to release into the patient's tissues.

One illustrative agent promotes, when applied to the patient's tissues in a pharmaceutically acceptable amount, well-organized collagenous tissue growth, such as scar tissue growth, preferably in large quantities. The tissue growth factor may include natural and/or recombinant proteins for stimulating a tissue response so that collagenous tissue growth, such as scar tissue growth, is enhanced. Exemplary growth factors that may be used include, but are not limited to, platelet-derived growth factor (PDGF), fibroblast growth factor (FGF), transforming growth factor-beta (TGF-beta), vascular endothelium growth factor (VEGF), activin/TGF and sex steroid, bone marrow growth factor, growth hormone, insulin-like growth factor 1, and combinations thereof. The agent may also include a hormone, including but not limited to estrogen, steroid hormones, and other hormones to promote growth of appropriate collagenous tissue such as scar tissue. The agent may also include stem cells or other suitable cells derived from the host patient. These cells may be fibroblast, myoblast, or other progenitor cells to mature into appropriate tissues.

According to other illustrative embodiments, the therapeutic agents may be, for example, anti-inflammatory agents, including steroidal and non-steroidal anti-inflammatory agents, analgesic agents, including narcotic and non-narcotic analgesics, local anesthetic agents, antispasmodic agents, growth factors, gene-based therapeutic agents, and combinations thereof.

Exemplary steroidal anti-inflammatory therapeutic agents (glucocorticoids) include, but are not limited to, 21-acetoxyprefnenolone, alclometasone, algestone, amicinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumehtasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol priopionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylaminoacetate, prednisone sodium phosphate, prednisone, prednival, prednylidene, rimexolone, tixocortal, triamcinolone, triamcinolone acetonide, triamcinolone benetonide, triamcinolone hexacetonide, and pharmaceutically acceptable salts thereof.

Exemplary non-steroidal anti-inflammatory therapeutic agents include, but are not limited to, aminoarylcarboxylic acid derivatives such as enfenamic acid, etofenamate, flufenamic acid, isonixin, meclofenamic acid, mefanamic acid, niflumic acid, talniflumate, terofenamate and tolfenamic acid; arylacetic acid derivatives such as acemetacin, alclofenac, amfenac, bufexamac, cinmetacin, clopirac, diclofenac sodium, etodolac, felbinac, fenclofenac, fenclorac, fenclozic acid, fentiazac, glucametacin, ibufenac, indomethacin, isofezolac, isoxepac, lonazolac, metiazinic acid, oxametacine, proglumetacin, sulindac, tiaramide, tolmetin and zomepirac; arylbutyric acid derivatives such as bumadizon, butibufen, fenbufen and xenbucin; arylcarboxylic acids such as clidanac, ketorolac and tinoridine; arylpropionic acid derivatives such as alminoprofen, benoxaprofen, bucloxic acid, carprofen, fenoprofen, flunoxaprofen, flurbiprofen, ibuprofen, ibuproxam, indoprofen, ketoprofen, loxoprofen, miroprofen, naproxen, oxaprozin, piketoprofen, pirprofen, pranoprofen, protizinic acid, suprofen and tiaprofenic acid; pyrazoles such as difenamizole and epirizole; pyrazolones such as apazone, benzpiperylon, feprazone, mofebutazone, morazone, oxyphenbutazone, phenybutazone, pipebuzone, propyphenazone, ramifenazone, suxibuzone and thiazolinobutazone; salicylic acid derivatives such as acetaminosalol, aspirin, benorylate, bromosaligenin, calcium acetylsalicylate, diflunisal, etersalate, fendosal, gentisic acid, glycol salicylate, imidazole salicylate, lysine acetylsalicylate, mesalamine, morpholine salicylate, 1-naphthyl salicylate, olsalazine, parsalmide, phenyl acetylsalicylate, phenyl salicylate, salacetamide, salicylamine o-acetic acid, salicylsulfiric acid, salsalate and sulfasalazine; thiazinecarboxamides such as droxicam, isoxicam, piroxicam and tenoxicam; others such as ε-acetamidocaproic acid, s-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole and tenidap; and pharmaceutically acceptable salts thereof.

Exemplary narcotic analgesic therapeutic agents include, but are not limited to, alfentanil, allylprodine, alphaprodine, anileridine, benzylmorphine, bezitramide, buprenorphine, butorphanol, clonitazene, codeine, codeine methyl bromide, codeine phosphate, codeine sulfate, desomorphine, dextromoramide, dezocine, diampromide, dihydrocodeine, dihydrocodeinone enol acetate, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, hydrocodone, hydromorphone, hydroxypethidine, isomethadone, ketobemidone, levorphanol, lofentanil, meperidine, meptazinol, metazocine, methadone hydrochloride, metopon, morphine, myrophine, nalbuphine, narceine, nicomorphine, norlevorphanol, normethadone, normorphine, norpipanone, opium, oxycodone, oxymorphone, papaveretum, pentazocine, phenadoxone, phenazocine, pheoperidine, piminodine, piritramide, proheptazine, promedol, properidine, propiram, propoxyphene, rumifentanil, sufentanil, tilidine, and pharmaceutically acceptable salts thereof.

Exemplary non-narcotic analgesic agents include, but are not limited to, aceclofenac, acetaminophen, acetaminosalol, acetanilide, acetylsalicylsalicylic acid, alclofenac, alminoprofen, aloxiprin, aluminum bis(acetylsalicylate), aminochlorthenoxazin, 2-amino-4-picoline, aminopropylon, aminopyrine, ammonium salicylate, amtolmetin guacil, antipyrine, antipyrine salicylate, antrafenine, apazone, aspirin, benorylate, benoxaprofen, benzpiperylon, benzydamine, bermoprofen, brofenac, p-bromoacetanilide, 5-bromosalicylic acid acetate, bucetin, bufexamac, bumadizon, butacetin, calcium acetylsalicylate, carbamazepine, carbiphene, carsalam, chloralantipyrine, chlorthenoxazin(e), choline salicylate, cinchophen, ciramadol, clometacin, cropropamide, crotethamide, dexoxadrol, difenamizole, diflunisal, dihydroxyaluminum acetylsalicylate, dipyrocetyl, dipyrone, emorfazone, enfenamic acid, epirizole, etersalate, ethenzamide, ethoxazene, etodolac, felbinac, fenoprofen, floctafenine, flufenamic acid, fluoresone, flupirtine, fluproquazone, flurbiprofen, fosfosal, gentisic acid, glafenine, ibufenac, imidazole salicylate, indomethacin, indoprofen, isofezolac, isoladol, isonixin, ketoprofen, ketorolac, p-lactophenetide, lefetamine, loxoprofen, lysine acetylsalicylate, magnesium acetylsalicylate, methotrimeprazine, metofoline, miroprofen, morazone, morpholine salicylate, naproxen, nefopam, nifenazone, 5' nitro-2' propoxyacetanilide, parsalmide, perisoxal, phenacetin, phenazopyridine hydrochloride, phenocoll, phenopyrazone, phenyl acetylsalicylate, phenyl salicylate, phenyramidol, pipebuzone, piperylone, prodilidine, propacetamol, propyphenazone, proxazole, quinine salicylate, ramifenazone, rimazolium metilsulfate, salacetamide, salicin, salicylamide, salicylamide o-acetic acid, salicylsulfuric acid, salsalte, salverine, simetride, sodium salicylate, sulfamipyrine, suprofen, talniflumate, tenoxicam, terofenamate, tetradrine, tinoridine, tolfenamic acid, tolpronine, tramadol, viminol, xenbucin, zomepirac, and pharmaceutically acceptable salts thereof.

Exemplary local anesthetic therapeutic agents include, but are not limited to, ambucaine, amolanone, amylocaine hydrochloride, benoxinate, benzocaine, betoxycaine, biphenamine, bupivacaine, butacaine, butaben, butanilicaine, butethamine, butoxycaine, carticaine, chloroprocaine hydrochloride, cocaethylene, cocaine, cyclomethycaine, dibucaine hydrochloride, dimethisoquin, dimethocaine, diperadon hydrochloride, dyclonine, ecgonidine, ecgonine, ethyl chloride, beta-eucaine, euprocin, fenalcomine, fomocaine, hexylcaine hydrochloride, hydroxytetracaine, isobutyl p-aminobenzoate, leucinocaine mesylate, levoxadrol, lidocaine, mepivacaine, meprylcaine, metabutoxycaine, methyl chloride, myrtecaine, naepaine, octacaine, orthocaine, oxethazaine, parethoxycaine, phenacaine hydrochloride, phenol, piperocaine, piridocaine, polidocanol, pramoxine, prilocaine, procaine, propanocaine, proparacaine, propipocaine, propoxycaine hydrochloride, pseudococaine, pyrrocaine, ropavacaine, salicyl alcohol, tetracaine hydrochloride, tolycaine, trimecaine, zolamine, and pharmaceutically acceptable salts thereof.

Exemplary antispasmodic therapeutic agents include, but are not limited to, alibendol, ambucetamide, aminopromazine, apoatropine, bevonium methyl sulfate, bietamiverine, butaverine, butropium bromide, n-butylscopolammonium bromide, caroverine, cimetropium bromide, cinnamedrine, clebopride, coniine hydrobromide, coniine hydrochloride, cyclonium iodide, difemerine, diisopromine, dioxaphetyl butyrate, diponium bromide, drofenine, emepronium bromide, ethaverine, feclemine, fenalamide, fenoverine, fenpiprane, fenpiverinium bromide, fentonium bromide, flavoxate, flopropione, gluconic acid, guaiactamine, hydramitrazine, hymecromone, leiopyrrole, mebeverine, moxaverine, nafiverine, octamylamine, octaverine, oxybutynin chloride, pentapiperide, phenamacide hydrochloride, phloroglucinol, pinaverium bromide, piperilate, pipoxolan hydrochloride, pramiverin, prifinium bromide, properidine, propivane, propyromazine, prozapine, racefemine, rociverine, spasmolytol, stilonium iodide, sultroponium, tiemonium iodide, tiquizium bromide, tiropramide, trepibutone, tricromyl, trifolium, trimebutine, n-trimethyl-3, 3-diphenyl-propylamine, tropenzile, trospium chloride, xenytropium bromide, and pharmaceutically acceptable salts thereof.

The agent(s) may be associated with the sling 36 in a variety of manners. For example, the agent may be chemically or physically attached to the surface of the sling 36. In one illustrative embodiment, one or more surfaces of the sling 36 and the agent, for example, in solution, have complementary ionic charges. As such, when placed on the sling 36, the agent ionically bonds to the one or more surfaces.

As mentioned above, the sling assembly 30 may include a sleeve 38. However, according to an alternative illustrative embodiment, the sling 36 may incorporate a protective treatment/coating, which is preferably biocompatible and may be bioabsorbable/dissolvable. Such protective treatments include, but are not limited to, alginates, sugar based formulations, starches, gelatins, cellulose, polyvinyl alcohol, polyglycolic acid (PGA), polylactic acid (PLA), polydioxinone (PDO), and/or other synthetic or natural polymers including combinations thereof. The treatment materials may cover any portion or all of the sling 36. In one particular configuration, the protective treatment encapsulates or substantially encapsulates at least a portion of the sling 36. According to one feature, the protective treatment is formed from lubricious material, which reduces the friction between the sling 36 and the patient's periurethral tissues. In this way, the protective treatment can provide a relatively smooth tissue contact surface to otherwise tanged or ragged sling edges to reduce the likelihood of the filament mesh sling 36 irritating the patient's tissues during implantation.

The protective treatment may be applied to the sling 36 by any suitable approach, for example, by way of spraying, brushing or dipping the portion of the sling 36 to be treated. According to another illustrative embodiment, the protective treatment is formed as a sheet of material that can be affixed to the portion of the sling 36 to be treated. According to another feature, the protective treatment may be configured to dissolve within a particular time range. The protective treatment may be configured, for example, to substantially absorb into the patient's tissues within about 5, 10, 15 or 30 minutes from the time the sling 36 is implanted. Alternatively, the protective treatment may be configured to substantially absorb into the patient's tissues over a time span of hours, days, weeks, or months.

In another illustrative embodiment, before application of the agent, the protective treatment is applied to the sling 36. According to another illustrative embodiment, the protective treatment and the agent are mixed to form a single treatment and then applied to the sling 36 in a one step process.

In the case of the illustrative embodiment, the sleeve 38 of sling assembly 30 is attached to a dilator shaft 40, which can be solid or have a lumen 42 extending therethrough. Like the delivery device 10, the sling assembly 30 may have a needle-shaped or blunt tip 41 formed on the distal end 34 of the dilator shaft 40 and shaped to enable tissue piercing or tissue dissection. The dilator shaft 40 may also have approximately the shape of a partial circle, for example between an eighth and a quarter circle. The dilator shaft 40 may have any shape suitable for the intended procedure, may include curved and straight section, and may be made of stainless steel or plastic, or any other suitable biocompatible material. The distal end 34 of the dilator shaft 40 is marked in FIG. 3 with a circular arrow "B" to indicate that it may include a connector of the type described in more detail below.

The dilator shaft 40 may be solid or may have a lumen 42 extending therethrough. In one embodiment, the distal end 34 of dilator shaft 40 may include a light-emitting device 44, such as a light-emitting diode (LED) or an optical fiber. The light-emitting element 44 may emit light 112 of any suitable color, such as white or red light. The emitted light should preferably have a wavelength that is not strongly absorbed by the patient's tissue, so as to be visible to a clinician. The LED may receive electric power through electric wires 46 passing through lumen 42. The wires may terminate at a connector 48 for connection to an external power source (not shown) or may connect to wires 49 extending at least partially through the sleeve 38, and terminate, for example, at an opposite end of the sleeve 38. Likewise, an optical fiber may pass through the lumen 42 and be coupled to a light source (not shown) either by an optical coupler/connector analogous to coupler 48 or extend further through the sleeve 38, for example as a fiber analogous to wires 49, and terminate, for example, at an opposite end of the sleeve 38.

Alternatively, the placement of the light-emitting element 44 and the translucent sleeve portion 23 may be reversed, so that the light-emitting element 44 is disposed near the distal end 20 of delivery device 10, while the translucent sleeve portion 23 is disposed near the distal end 34 of dilator shaft 40. An exemplary reversed arrangement will be described below with reference to FIG. 9.

Figure 5:
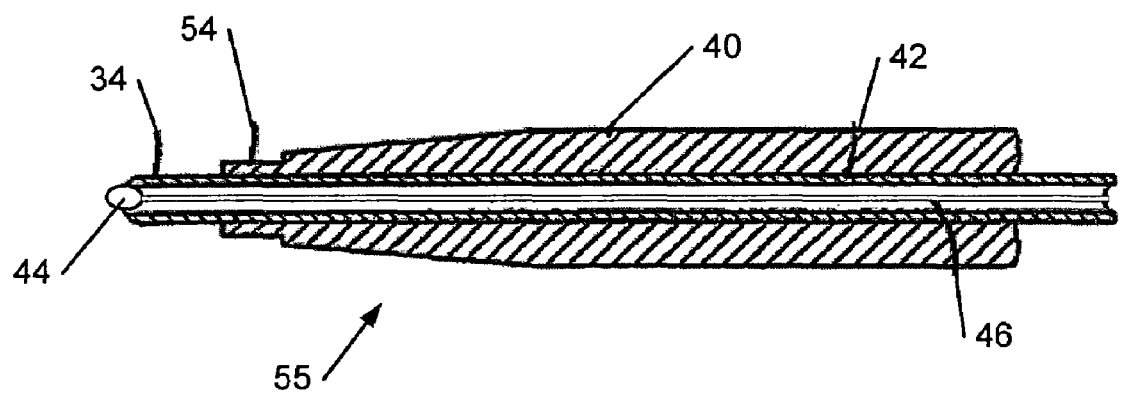
FIG. 5 shows a complementary connector for the delivery device of FIG. 3.

As indicated in FIGS. 1 to 3 by arrows "A" and "B", respectively, the distal end 20 of guide tube 14 and the distal end 34 of sling assembly 30 may each include or be fitted with mating terminations or connectors, which releasably or non-releasably interlock the delivery device 10 with the sling assembly 30. FIG. 4 shows an exemplary connector 50 integrally formed on or attached to the distal end 20 of guide tube 14. Also shown in FIG. 4 is the shaft 12 with the tip 13, which can be extended to a position 53 for dissecting/piecing the patient's tissue and retracted to a position 51 by operating actuator 22 on handle 16. FIG. 5 shows a mating connector 55 integrally formed on or attached to the distal end 34 sling assembly 30. The connectors 50 and 55 have respective lockable, mating engaging surfaces 52, 54, examples of which are described, for example, in commonly assigned U.S. patent application Ser. No. 10/641487, the contents of which is hereby incorporated herein by reference in its entirety. When the tip 13 of shaft 12 is retracted to position 51, the male connector 55 of FIG. 5 can engage and interlock with the female connector 50 of FIG. 4, as illustrated in FIG. 6. When the two connectors 50, 55 are interlocked, the light-emitter 44 is positioned inside the translucent sleeve portion 23. The colored translucent sleeve portion 23 may then operate as an optical filter, so that the color of the radiated light changes upon successful coupling between connectors 50 and 55. Alternatively, a change in the intensity of the emitted light could also be an indication of engagement between the connectors 50, 55. This will be described in more detail below.

The connection between connectors 50 and 55 can be mechanical, for example, by forming engaging recesses and projections on the connectors 50, 55, for example, in the form of grooves, indentations, openings, and the like, adapted to engage with protrusions, tongues, and the like. The connectors 50, 55 may be releasable or non-releasable, with the connection being at least strong enough so that the delivery device 10 does not separate from the sling assembly 30 when the connected delivery device 10 and the sling 30 are pulled through the patient's membranes and body tissue. The delivery device 10 may be separated from the sling assembly 30 once the sling assembly 30 is inserted in the patient.

While the complementary connectors 50, 55 in the illustrative embodiments of FIGS. 1-5 are shown as mechanically interlocked male and female connectors, those skilled in the art will appreciate that a number of alternative configurations can be employed for the connectors, such as magnetic forces produced by small permanent magnets disposed on or in the respective tips, and the present invention contemplates such alternative configurations. The configuration of the connectors 50, 55 can also be reversed, as mentioned above.

Figure 6:
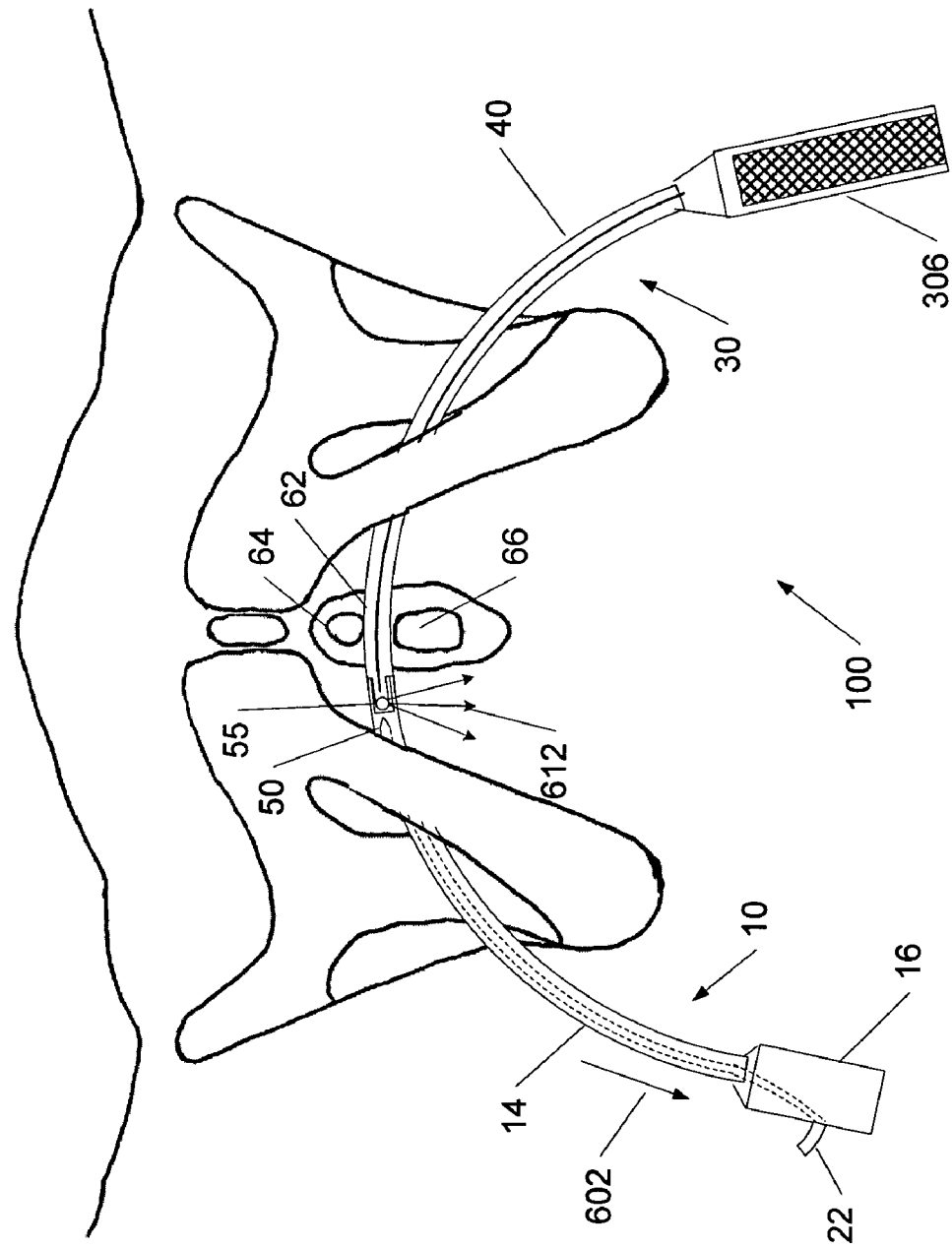
FIG. 6 shows a perspective front view of the sling delivery device with interconnected delivery device and sling assembly according to the invention.

FIG. 6 shows the delivery assembly 100 with the delivery device 10 interlocked with the sling assembly 30. As described above with reference to FIG. 1, the light emitted by light emitter 44 before the device sections are joined should be observable by the clinician through the vaginal wall, for example, as white light 112 (FIG. 1). When the connector 55 of sling assembly 30 interfits with the connector 50 of the delivery device 10, the light 112 passes through the translucent sleeve section 23 which may be colored, for example red. Accordingly, when the delivery device 10 interlocks with the sling assembly 30 in the space 62 between the urethra 64 and the vaginal wall 66, the clinician will notice a color change in the light emission 612 (see FIG. 6) at the connection point between the delivery device 10 and the sling assembly 30.

The invention may advantageously be employed with a transobtural implantation procedure. In one such transobtural procedure, the procedure is prepped by injecting a local anesthetic at the obturator membranes, and lidocaine suburethrally to hydro-dissect the pelvic tissue. A Foley catheter is placed in the bladder to identify the bladder neck. The delivery device 10 is introduced through an incision in the ischiopubic region and passed through an obturator foramen into the space 62 between the urethra 64 and the vaginal wall 66, without puncturing the vaginal wall.

The surgeon locates by feel the general area of the obturator through the vaginal wall. The surgeon then locates the same location at the transobturator incision point and pierces the obturator membrane, for example, with the extended tip 13 (see, for example, FIG. 2) of delivery device 10. After piercing the membrane, the delivery device 10 will come in contact with the elastic upper vaginal wall and can be felt by the surgeon. The surgeon can use his/her finger as a guide and maintain contact with distal end 20 of the guide tube 14 and/or the connector 50 on the other side of the vaginal wall and guide the distal end 20 to the suburethral position, as determined by the midpoint between the meatus of the urethra and the location of the inflated Foley balloon, preferably about one centimeter beyond the midpoint.

The aforedescribed procedure is then repeated contralaterally with the sling assembly 30, which is introduced through a second incision in the ischiopubic region and passed through the other obturator foramen and into the space 62 between the urethra 64 and the vaginal wall 66. The tip 41 disposed on the distal end 34 of dilator shaft 40 (see, for example, FIG. 3) and optionally including the light emitter 44 is provided for cutting through the tissue. After piercing the obturator membrane, the tip 41 and/or connector 55 of the dilator shaft 40 will come in contact with the elastic upper vaginal wall and can be felt by the surgeon. The surgeon can use his/her finger as a guide and maintain contact with the tip 41 and/or the connector 55 on the other side of the vaginal wall and guide the tip 41 to a position proximate to the position of tip 13 of delivery device 10. The delivery device 10 and the sling assembly 30 can then be urged into locking engagement by applying pressure between, for example, the handle 16 of delivery device 10, and the proximal end 32 of the sling assembly 30. As mentioned before, proper engagement between the delivery device 10 and the sling assembly 30 can be visually observed by the resulting color change of light emission from a first color emitted as light 112 (FIG. 1) to a second, filtered color emitted as light 612 (FIG. 6).

As shown in FIG. 6, following the completion of the aforedescribed procedure, the coupled delivery assembly 100 formed of the delivery device 10 and sling assembly 30 forms a continuous, more or less U-shaped implement, with its center portion located approximately suburethrally above the upper vaginal wall. The connected U-shaped delivery system 100 can now be removed from the patient's body, for example, by pulling on handle 16 in the direction of arrow 602. This will pull along the sling assembly 30, including the sling or mesh 36 and the sleeve 38, if employed, through the continuous passage between the ischiopubic incisions.

The sleeve 38, if employed, can now be removed, leaving only the mesh 36 in place. The mesh 36 can be tensioned by administering a cough test and adjusting the mesh accordingly.

Figure 7:
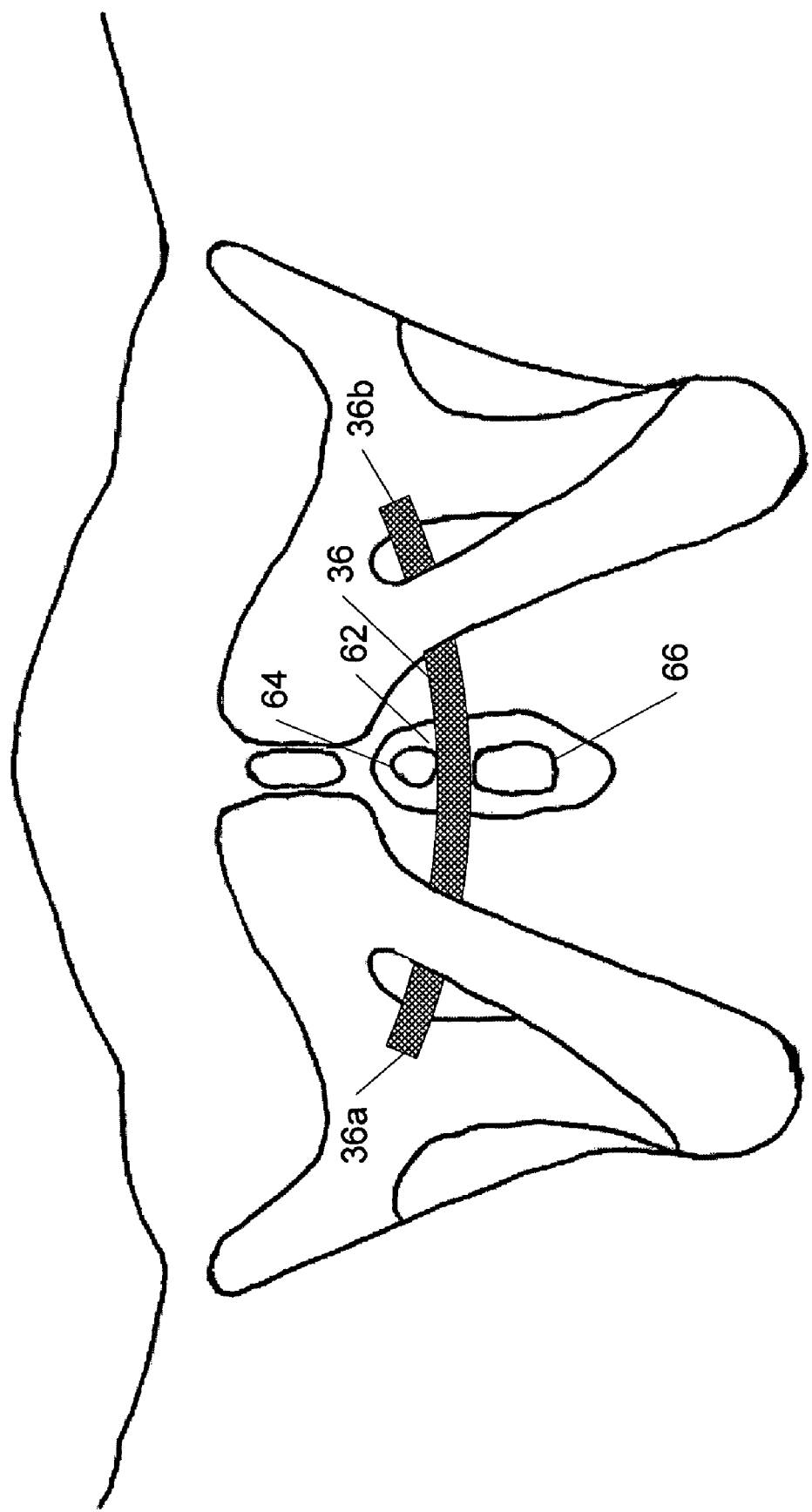
FIG. 7 shows a suburethrally implanted supporting mesh.

FIG. 7 shows schematically a mesh 36 implanted suburethrally and affixed to the obturator membranes. According to the illustrative embodiment, the mesh 36 is from about 1 to 3 cm in width and from about 10 to 45 cm in length, and terminates at free ends. The mesh 36 is shown to be rectangular, but it may have another suitable shape. The mesh 36 may have a uniform thickness over its entire length and/or width. Alternatively, the thickness can be suitably varied at one or more locations. According to the illustrative embodiment, the thickness of the mesh 36 material ranges from about 0.02 to about 0.10 cm. The end portions 36a, 36b of mesh 36 may be anchored in the obturator membranes, either with or without anchors, for example, with the tanged mesh portions described below.

In the illustrative embodiment, the mesh 36 is made entirely of polypropylene. However, mesh 36 may be fabricated from any of a number of biocompatible materials, such as nylon, polyethylene, polyester, polypropylene, fluoropolymers, copolymers thereof, combinations thereof, or other suitable synthetic material(s). The material may be, for example, a synthetic material that is absorbable by the patient's body, such as polyglycolic acid, polylactic acid, and other suitable absorbable synthetic materials. Alternatively, the material for the mesh 36 may be derived from mammalian tissue(s) or a combination of mammalian tissue(s) and synthetic material(s). The sling material may be fabricated from one or more yarns, which yarns may be made from one or more materials. The mesh 36 may incorporate or be coated with one or more agents to provide a therapeutic effect, for example, to reduce discomfort, to reduce the chance of infection and/or to promote tissue growth.

As mentioned above, in one exemplary embodiment, the length of the sling or mesh 36 is shorter than the length of the sleeve 38, and the mesh 36 does not connect to the sleeve 38 or anything else. This feature inhibits the medical operator from gripping the free ends of the sling assembly 30 and inadvertently tensioning the mesh 36. This feature may be further enhanced by making the mesh 36 long enough to support the urethra, but not long enough to expose the ends 36a and 36b of the sling outside the body. This has the advantage of preventing infection caused by the exposure of the mesh 36 external to the body. By way of example, an illustrative sleeve 38 may be between about 1 cm and 30 cm longer than the mesh 36. In particular, in transobtural procedures, the mesh 36 may be configured to be long enough to extend to, or through, both obturator foramen, but not long enough to extend outside of the body. In other embodiments, the mesh 36 may be configured in length to extend outside of the body, when placed, and the ends then trimmed to length by the physician to a point just under the skin.

In one illustrative embodiment, the edge regions of the mesh 36 can be configured differently depending on their intended placement in the body of the patient. For example, a midsection of the mesh 36 is typically located where an anatomical site, such as a mid-urethral or bladder neck location in the periurethral tissue, needs to be supported. In one embodiment, the midsection of the mesh 36 has smooth or rounded edges, hereinafter also referred to as "non-tanged" or "de-tanged." According to a further illustrative embodiment, other sections of the sling may include tangs (e.g., sharp projections or frayed edges). The tangs are generally useful for anchoring the mesh 36 and/or encouraging tissue growth into the sling. Anchoring the mesh 36 in this manner generally obviates the need for additional anchors or sutures to hold the sling in place.

The tanged and non-tanged edges of the mesh 36 can be formed in a plurality of ways. For example, the mesh 36 can be cut from a woven sheet, in which case the edges would be initially tanged along the entire length of the sling. One or more non-tanged sections may be formed by any process that smoothes, rounds or removes the sharp edges of the tangs. For example, the tangs may be heat-smoothed by burning or melting the tangs. In one embodiment, the non-tanged section has a length of about 1 to about 5 cm, preferably about 2 to about 2.5 cm, on either or both sides of the center line of the sling. Providing one or more non-tanged sections, which may be in close proximity to a sensitive anatomical site in the patient, can enhance the comfort level of the patient and reduce the potential for the edges of the tangs to erode or irritate the urethra. Alternatively, the mesh 36 can be produced from a woven tape having the approximate finished width of the sling. The smooth sides of the tape can then be trimmed off to produce the tanged sections.

The mesh or sleeve could be provided with measurement markings that would indicate to the clinician a particular position or location preferred for placement of the mesh, such as the center of the mesh. For example, the de-tanged mesh section should be located suburethrally.

According to another feature, successful engagement between delivery device 10 and sling assembly 30 can be verified with devices other than optical devices, such as resistive, capacitive and/or inductive electrical devices and/or sensors disposed on or proximate to the connectors 50, 55. For example, the translucent sleeve 23 disposed on the distal end 20 of guide tube 14 (see FIGS. 2 and 4) may incorporate or be replaced with a resistive region, windings of a coil or capacitive plates. The electrical resistance could be monitored with an ohmmeter installed in or attached to, for example, the handle 16 and connected by wires to a contact pad in the connector 55. Engagement between the connectors 50 and 55 could result in a lowering of the electrical resistance between the wires. In another exemplary embodiment, a switch may be incorporated in one of the connectors 50, 55 which may be actuated as a result of the mechanical engagement between the connectors 50, 55. Alternatively or in addition, the inductance of the coil or the capacitance between the plates could be monitored with, for example, a tuned circuit which may be battery-powered and enclosed in the handle 16 or otherwise connected to the handle 16. The light emitter 44 could then be omitted and replaced with, for example, a material, such as metal or another material with a magnetic susceptibility or dielectric constant sufficient different from that of the human body tissue. Alternatively, the tip 41 may be made of such a material. When the delivery device 10 and sling assembly 30 are coupled at their respective distal end by the modified connectors 50, 55, the resonance frequency of the tuned circuit changes. This change in the resonance frequency could then be identified by the clinician, for example, through an audible (e.g., a change in frequency of a tone produced by a loudspeaker) and/or visual signal.

Figure 8:
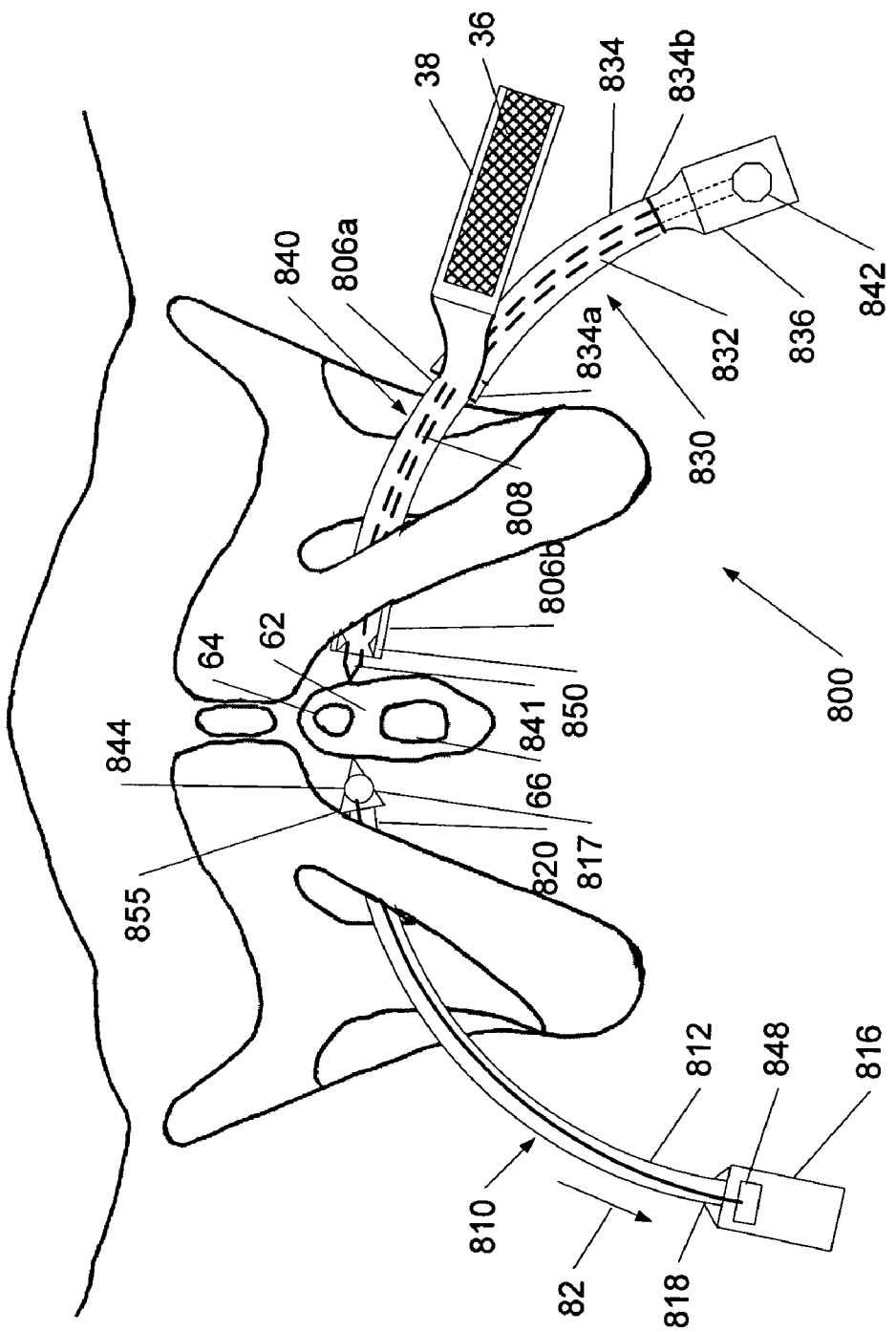
FIG. 8 shows another embodiment of a sling delivery assembly with a dilator and pusher assembly.

FIG. 8 shows another illustrative embodiment of a delivery assembly 800 according to the invention. The delivery assembly 800 includes a delivery device 810 with a handle 816 associated with a curved shaft 812. The shaft 812 has a proximal end 818 attached to the handle 816 and a distal end 820 which includes a fixed tip 817 suitable for separating and/or piercing tissue, and a coupler 855 adapted to couple with a mating coupler 850 disposed on the distal end 806b of a dilator tube 840. The proximal end 806a of dilator tube 840 is operatively connected to a sling or mesh 36 which may be enclosed in a sleeve 38, as described above. The connector 855 can be constructed similarly to the connector 55 (FIG. 5) and may include a light emitter 844. In all other aspects, light emitter 844 can be implemented as and connected like light emitter 44, i.e. as an LED or optical fiber, with an electrical or optical connection 848 integrated in or connected to the handle 816. For example, handle 816 may include a connector 848 (electrical or optical) on the handle, or alternatively, the light source or a battery for the light source (not shown) may be incorporated in the handle 816. The shaft 812 may be, for example, any suitable needle, cannula, tubular member, tunneler, dilator and the like, and may be made of a rigid or semi-rigid material, for example, metal or plastic.

The shaft 832 of a pusher assembly 830 slidably interfits inside dilator tube 840. The dilator tube 840 may be flexible and made of a bio-compatible plastic. The pusher assembly 830 includes, in addition to shaft 832, a pusher tube 834 having a distal end 834a and a proximal end 834b, a handle 836, a pusher button 842, and a pusher tip 841 disposed in the distal end of shaft 832 for aiding in the dissection of tissue. In the assembled state, the pusher tube 834 and the pusher button 842 are slidably moveable over the shaft 832. Other elements of the pusher assembly 830 which are not part of the invention, have been omitted for sake of clarity. A pusher assembly of this type is described, for example, in commonly assigned U.S. patent application Ser. No. 10/641,487, the contents of which is hereby incorporated herein by reference in its entirety. The pusher assembly 830 facilitates the insertion of the dilator tube 840 through the obturator membrane 808 and coupling to the delivery device 810.

The connector 850 may be constructed similar to connector 50 of FIG. 5. For example, connector 850 may be translucent or include at least a translucent sleeve portion 23. As in the embodiment described above with reference to FIGS. 1 and 4, the delivery device 810 and the dilator tube 840 are securely connected, when the light emitted by the light emitter passes through the translucent sleeve section 23 which is preferably colored. Accordingly, proper engagement between the delivery device 810 and the dilator tube 840 can be determined, for example, from a change in the color of the light emission at the connection point between the connectors 850 and 855. This change in color can be detected by the clinician through the patient's tissue, for example, the vaginal wall.

The locking engagement between connectors 850, 855 may be non-releasable, or should be at least strong enough so that the delivery device 810 and the dilator tube 840 do not separate when the delivery device 810 and the dilator tube 840 with the sleeve 38 and sling 36 are pulled through the patient's obturator membrane and body tissue. The pusher tip 841 is retracted into the dilator tube 840 by operating pusher button 842, once the connector 855 is located in the space 62 between the urethra 64 and the vaginal wall and before the connector 850 is coupled to connector 855 of the delivery device 810.

While the complementary connectors 850 and 855 in FIG. 8 are shown as male and female connectors, those skilled in the art will appreciate that a number of alternative configurations can be employed for the engaging members, such as magnetic forces produced by small permanent magnets disposed on or in the respective tips, and the present invention contemplates such alternative configurations. Moreover, the order or arrangement of the engaging members may be reversed and/or any type of interlocking mechanisms, such as recesses, projections, tongues, resilient elements, electromagnetic forces, vacuum connections and the like, can be employed without limitation.

In a transobtural procedure using the delivery assembly 800, the procedure is prepped as before and the dilator tube 840 with the attached sling 36 and sleeve 38, if employed, are introduced through an incision in the ischiopubic region and pushed, with pusher tip 841 protruding from the distal end 806b of dilator tube 840, by pusher assembly 830 toward and through an obturator foramen and into the space 62 between the urethra 64 and the vaginal wall 66. The procedure then continues by introducing the delivery device 810 contralaterally through a second incision in the ischiopubic region and through the other obturator foramen. The surgeon can use his/her finger as a guide and maintain contact with, for example, the tip 817 and guide the tip 817 to a position proximate to the distal end 806B of dilator tube 840. The shaft 832 is then retracted into the dilator tube 840 by actuating the pusher button 842, causing the distal end 834a of pusher tube 834 to apply a force to proximal end 806a of dilator tube 840. Dilator tube 840 then slides over pusher shaft 832 over pusher tip 841, thus enabling the connector 850 to slide into the connector 855 for locking engagement therebetween.

The dilator tube 840 with the attached sling 36 and sleeve 38 can now be pulled, as described above, through the continuous body passage created by the delivery device 810 and the pusher assembly 830 between the two ischiopubic incisions, for example, by pulling on handle 836 in the direction of arrow 82.

It should be pointed out that the delivery assembly 800 may also be used in a percutaneous sling implantation.

FIG. 9 shows another conceptual embodiment of a sling delivery assembly 900 which includes a single curved shaft 910 sized and shaped to be pushed, for example, in the direction of arrow 902 from a first incision in the ischiopubic region through one obturator foramen into the space 62 between the urethra 64 and the vaginal wall 66, and from there through the other obturator foramen, exiting at a first incision in the contralateral ischiopubic region. As in the first embodiment described above, for example, with reference to FIG. 1, a sling 36, optionally enclosed in a sleeve 38, is attached to proximal end 912 of the shaft 910. The distal end of the shaft 910 includes a dilator or dissection tip 914.

Following the completion of the preceding procedures, either percutaneous or through the obturator membranes, the sling or mesh 36 is now located in the tissue 62 between the urethra 64 and the upper vaginal wall 66. No transvaginal incisions are required. The sling or sutures or integral attachment members extending therefrom may be sewn, stapled, riveted, or anchored to any of a variety of structures, such as the pubic bone, Cooper's ligament or rectus fascia to stabilize or stabilize the bladder neck or to stabilize the pelvic floor. For example, a long sling may be attached directly to the pubic periosteum using staples, clips, or sutures or may be attached to the pubic bone with short sutures attached to a bone anchor implanted in the pubic bone or fastened to the pubic bone with a headed nail or screw-like anchoring device.

The aforedescribed sling delivery device devices, guide tubes and/or dilators may have a diameter between about 0.05" (about 1.25 mm) and about 0.3" (about 7.5 mm). Physicians prefer devices of smaller diameter, because these tend to cause less tissue disruption. Conversely, larger diameter devices have increased mechanical strength and can more easily be joined in the tissue by feel because of the greater range for associating the two delivery devices.

While the invention has been disclosed in connection with the preferred embodiments shown and described in detail, various modifications and improvements thereon may be made thereto without departing from the spirit and scope of the invention. By way of example, although the illustrative embodiments are depicted as providing support of the urethra or bladder neck to alleviate discomfort form urinary incontinence in women, this need not be the case. Although the illustrative embodiments are depicted in conjunction with a transobtural implantation, the sling delivery device of the invention may also be inserted percutaneously into the body without making a trans-vaginal incision. Also, the described devices, methods and procedures can also be used to treat male incontinence or to support other weakened tissue or muscles in the body.

Other variations, modifications, and implementations of what is described may also occur without departing from the spirit and the scope of the invention. By way of example, and without limitation, examples of slings, sling assemblies, sling delivery devices and approaches, sling assembly-to-delivery device association mechanisms, and sling anchoring mechanisms including features that may be employed with the above described invention are disclosed in U.S. Pat. No. 6,042,534, entitled "Stabilization sling for use in minimally invasive pelvic surgery," U.S. Pat. No. 6,755,781, entitled "Medical slings," U.S. Pat. No. 6,666,817, entitled "Expandable surgical implants and methods of using them,"U.S. Pat. No. 6,042,592, entitled "Thin soft tissue surgical support mesh," U.S. Pat. No. 6,375,662, entitled "Thin soft tissue surgical support mesh," U.S. Pat. No. 6,669,706, entitled "Thin soft tissue surgical support mesh," U.S. Pat. No. 6,752,814, entitled "Devices for minimally invasive pelvic surgery," U.S. Ser. No. 10/918,123, entitled "Surgical Slings," U.S. patent application Ser. No. 10/641,376, entitled "Spacer for sling delivery system," U.S. patent application Ser. No. 10/641,192, entitled "Medical slings," U.S. Ser. No. 10/641,170, entitled "Medical slings," U.S. Ser. No. 10/640,838, entitled "Medical implant," U.S. patent application Ser. No. 10/460,112, entitled "Medical slings," U.S. patent application Ser. No. 10/631,364, entitled "Bioabsorbable casing for surgical sling assembly," U.S. Ser. No. 10/092,872, entitled "Medical slings," U.S. patent application Ser. No. 10/939,191, entitled "Devices for minimally invasive pelvic surgery," U.S. patent application Ser. No. 10/774,842, entitled "Devices for minimally invasive pelvic surgery," U.S. patent application Ser. No. 10/774,826, entitled "Devices for minimally invasive pelvic surgery," U.S. Ser. No. 10/015,114, entitled "Devices for minimally invasive pelvic surgery," U.S. patent application Ser. No. 10/973,010, entitled "Systems and methods for sling delivery and placement," U.S. patent application Ser. No. 10/957,926, entitled "Systems and methods for delivering a medical implant to an anatomical location in a patient," U.S. patent application Ser. No. 10/939,191, entitled "Devices for minimally invasive pelvic surgery," U.S. patent application Ser. No. 10/918,123, entitled "Surgical slings," U.S. patent application Ser. No. 10/832,653, entitled "Systems and methods for sling delivery and placement," U.S. patent application Ser. No. 10/642,397, entitled "Systems, methods and devices relating to delivery of medical implants," U.S. patent application Ser. No. 10/642,395, entitled "Systems, methods and devices relating to delivery of medical implants," U.S. patent application Ser. No. 10/642,365, entitled "Systems, methods and devices relating to delivery of medical implants," U.S. patent application Ser. No. 10/641,487, entitled "Systems, methods and devices relating to delivery of medical implants," U.S. patent application Ser. No. 10/094,352, entitled "System for implanting an implant and method thereof," U.S. patent application Ser. No. 10/093,498, entitled "System for implanting an implant and method thereof," U.S. patent application Ser. No. 10/093,450, entitled "System for implanting an implant and method thereof," U.S. patent application Ser. No. 10/093,424, entitled "System for implanting an implant and method thereof," U.S. patent application Ser. No. 10/093,398, entitled "System for implanting an implant and method thereof," and U.S. patent application Ser. No. 10/093,371, entitled "System for implanting an implant and method thereof," the entire contents of all of which are incorporated herein by reference.

Accordingly, the spirit and scope of the present invention is to be limited only by the following claims.

What is claimed is:

1. A sling delivery assembly comprising:
    a delivery device having a guide tube with a proximal end and a distal end, a shaft slidingly interfitted in the guide tube, and a first connector attached to or integrally formed with the distal end of the guide tube;
    a sling assembly having a proximal end and a distal end, and a second connector attached to or integrally formed with the distal end of the sling assembly and adapted for interlocking engagement with the first connector; and
    an indicator formed in or on the first or second connector, or both, to indicate interlocking engagement between the first and second connector;
    wherein the indicator comprises a light emitter disposed on one of the first or second connectors, and an optically transmissive element formed on the other connector;
    wherein
        an observed color of light emitted from the light emitter changes upon engagement between the first and second connector, or
        an observed intensity of light emitted from the light emitter changes upon engagement between the first and second connector.

2. The sling delivery assembly of claim 1, wherein the delivery device comprises a dilator tip or tissue dissector disposed on a distal end of the shaft.

3. The sling delivery assembly of claim 1, wherein the delivery device comprises:
    a handle disposed on a proximate end of the delivery device; and
    an actuator disposed on or in the handle for causing the dilator tip or tissue dissector to protrude from and be retracted into the distal end of the guide tube.

4. The sling delivery assembly of claim 1, wherein the shaft of the delivery device is at least partially curved.

5. The sling delivery assembly of claim 1, wherein the connectors comprise a mechanical interlocking mechanism.

6. The sling delivery assembly of claim 1, wherein the connectors comprise a magnetic interlocking mechanism.

7. The sling delivery assembly of claim 1, wherein the sling assembly comprises a sling or sleeve secured to the proximal end of the sling assembly.

8. The sling delivery assembly of claim 7, wherein the sling assembly comprises a sleeve secured to the proximal end of the sling assembly and a mesh which is free floating inside the sleeve.

9. The sling delivery assembly of claim 1, wherein the sling assembly includes a dilator tube with a proximal end and a distal end and a lumen.

10. The sling delivery assembly of claim 9, wherein the sling assembly includes a sling or sleeve attached to the proximal end of the dilator tube.

11. The sling delivery assembly of claim 10, wherein the sling assembly includes a sleeve attached to the proximal end of the dilator tube and a mesh which is free floating inside the sleeve.

12. A sling delivery assembly comprising:
    a delivery device having a guide tube with a proximal end and a distal end, a shaft slidingly interfitted in the guide tube, and a first connector attached to or integrally formed with the distal end of the guide tube;
    a sling assembly having a proximal end and a distal end, and a second connector attached to or integrally formed with the distal end of the sling assembly and adapted for interlocking engagement with the first connector; and
    an indicator formed in or on the first or second connector, or both, to indicate interlocking engagement between the first and second connector;
    wherein
        the indicator comprises a resistive element disposed on one of the first or second connectors, and a contact pad formed on the other connector and contacting the resistive element upon engagement between the first and second connector, or
        the indicator comprises a switch disposed on one of the first or second connectors, said switch being actuated upon engagement between the first and second connector, or
        the indicator comprises an inductive element disposed on one of the first or second connectors, and a sensor disposed on the other connector and detecting a change in an inductance upon engagement between the first and second connector, or
        the indicator comprises a capacitive element disposed on one of the first or second connectors, and a sensor detecting a change in a capacitance upon engagement between the first and second connector.

13. A sling delivery assembly comprising:
    a delivery device having a shaft with a proximal end and a distal end, and a first connector attached to or integrally formed with the distal end of the shaft;
    a sling assembly having a dilator tube with a proximal end and a distal end and a lumen, a sling or sleeve attached to the proximal end of the dilator tube and a second connector attached to or integrally formed with the distal end of the dilator tube, said second connector adapted for interlocking engagement with the first connector; and
    an indicator formed in or on the first or second connector, or both, to indicate interlocking engagement between the first and second connector;
    wherein the indicator comprises a light emitter disposed on one of the first or second connectors, and an optically transmissive element formed on the other connector;
    wherein
        an observed color of light emitted from the light emitter changes upon engagement between the first and second connector, or
        wherein an observed intensity of light emitted from the light emitter changes upon engagement between the first and second connector.

14. The sling delivery assembly of claim 13, comprising:
    a pusher assembly having a pusher shaft with a pusher tip, said pusher shaft slidingly interfitting inside the lumen of the dilator tube and a pusher tube having a distal end adapted to make contact with the proximal end of the dilator tube for moving the pusher tip into a retracted position inside the lumen of the dilator tube, to enable the interlocking engagement between the first and second connector.

15. The sling delivery assembly of claim 13, wherein the connectors comprise a mechanical interlocking mechanism.

16. The sling delivery assembly of claim 13, wherein the connectors comprise a magnetic interlocking mechanism.

17. The sling delivery assembly of claim 13, wherein the sling assembly comprises a sling or sleeve secured to the proximal end of the dilator tube.

18. The sling delivery assembly of claim 17, wherein the sling assembly comprises a sleeve secured to the proximal end of the dilator tube and a mesh which is free floating inside the sleeve.

19. The sling delivery assembly of claim 13, wherein the delivery device includes a guide tube with a proximal end and a distal end.

20. The sling delivery assembly of claim 19, wherein the shaft is slidingly interfitted in the guide tube.

21. A sling delivery assembly comprising:
a delivery device having a shaft with a proximal end and a distal end, and a first connector attached to or integrally formed with the distal end of the shaft;
a sling assembly having a dilator tube with a proximal end and a distal end and a lumen, a sling or sleeve attached to the proximal end of the dilator tube, and a second connector attached to or integrally formed with the distal end of the dilator tube, said second connector adapted for interlocking engagement with the first connector; and
an indicator formed in or on the first or second connector, or both, to indicate interlocking engagement between the first and second connector;
wherein
the indicator comprises a resistive element disposed on one of the first or second connectors, and a contact pad formed on the other connector and contacting the resistive element upon engagement between the first and second connector, or
the indicator comprises a switch disposed on one of the first or second connectors, said switch being actuated upon engagement between the first and second connector, or
the indicator comprises an inductive element disposed on one of the first or second connectors, and a sensor disposed on the other connector and detecting a change in an inductance upon engagement between the first and second connector, or
the indicator comprises a capacitive element disposed on one of the first or second connectors, and a sensor detecting a chance in a capacitance upon engagement between the first and second connector.

22. A method of treating urinary incontinence by implanting a surgical sling into the body of a patient without a transvaginal incision, comprising:
a) inserting a sling assembly having a sling associated therewith through a first transobturator incision point of a patient;
b) inserting a delivery device couplable to the sling assembly through a second contralateral transobturator incision point of a patient;
c) engaging the delivery device with the sling assembly at a connection location;
d) verifying interlocking engagement between the delivery device and the sling assembly through a change in an optical or electrical signal produced at the connection location; and
e) pulling the interlocked delivery device and sling assembly through periurethral tissue of the patient.

* * * * *